United States Patent [19]

Fujii et al.

[11] 4,324,742

[45] Apr. 13, 1982

[54] PROCESS FOR SEPARATION OF NAPHTHALENEDISULFONIC ACIDS

[75] Inventors: Hironory Fujii; Thuyoshi Nagashima; Nobuyori Shibamoto, all of Wakayama, Japan

[73] Assignee: Sugai Chemical Industry Co., Ltd., Wakayama, Japan

[21] Appl. No.: 180,895

[22] Filed: Aug. 25, 1980

Related U.S. Application Data

[63] Continuation-in-part of Ser. No. 48,247, Jun. 13, 1978, abandoned.

[30] Foreign Application Priority Data

Jun. 15, 1978 [JP] Japan .................................. 53-72622

[51] Int. Cl.$^3$ ............................................. C07C 143/24
[52] U.S. Cl. ............................ 260/505 C; 260/505 P
[58] Field of Search ....................... 260/505 C, 505 P

[56] References Cited

U.S. PATENT DOCUMENTS 2,125,189 7/1938 Lofton et al. .................. 260/505 C

FOREIGN PATENT DOCUMENTS 2028308 5/1980 United Kingdom ............ 260/505 C

*Primary Examiner*—Alan Siegel
*Attorney, Agent, or Firm*—Armstrong, Nikaido, Marmelstein & Kubovcik

[57] ABSTRACT

A process for separating 1,6-naphthalenedisulfonic acid, 2,6-naphthalenedisulfonic acid or 2,7-naphthalenedisulfonic acid selectively from reaction mixtures obtained by disulfonation of naphthalene under different reaction conditions is disclosed. For example, a particular disulfonation reaction of naphthalene is carried out which favors the formation of a particular isomer. This reaction mixture is diluted with water to adjust the sulfuric acid concentration to 35 to 90% by weight and the temperature is maintained at 0° to 80° C.; 1,6-naphthalene-disulfonic acid is selectively separated at high purity.

10 Claims, No Drawings

PROCESS FOR SEPARATION OF NAPHTHALENEDISULFONIC ACIDS

This application is a continuation-in-part of Ser. No. 048,247 filed June 13, 1978 now abandoned.

BACKGROUND OF THE INVENTION

1. Field of the Invention

The present invention relates to a novel process for separation of naphthalenedisulfonic acids. More particularly, the invention relates to a process for separating 1,6-naphthalenedisulfonic acid, 2,6-naphthalenedisulfonic acid or 2,7-naphthalenedisulfonic acid selectively from reaction mixtures obtained by disulfonation of naphthalene according to known disulfonation reactions which favor the formation of a particular isomer.

2. Description of the Prior Art

As is well known in the art, naphthalenedisulfonic acids are important and valuable intermediates for use in the manufacture of dyes, organic pigments, medicines and agricultural chemicals.

Generally, naphthalenedisulfonic acids can easily be prepared by sulfonation of naphthalene with a sulfonating agent such as sulfuric acid, fuming sulfuric acid or chlorosulfonic acid. When naphthalene is sulfonated at 80° C., the product is chiefly 1-naphthalene sulfonic acid. When it is sulfonated at 160° C. or higher, the yield is chiefly 2-naphthalene sulfonic acid. When the 1-naphthalene sulfonic acid is heated in sulfuric acid at 160° C., it is largely converted to the 2-isomer. The alpha-sulfonation occurs more rapidly because of the more stable intermediate carbonium ion. Sulfonation at the beta position occurs more slowly but, once formed, the beta-sulfonic acid tends to resist disulfonation.

At low temperatures, disulfonation is slow. Therefore, the isolated product is the product which is formed faster, i.e., the alpha-naphthalene sulfonic acid. At higher temperatures, the disulfonation becomes a more important factor, equilibrium is more readily established and the isolated product is the more stable beta-naphthalene sulfonic acid. At low temperatures, the controlling factor is the rate of reaction whereas, at high temperatures, the controlling factor becomes the position of equilibrium.

By controlling the various reaction parameters, the applicants are able to produce a disulfonated naphthalene which contains a high concentration of a particular isomer of the disulfonated naphthalene. However, the disulfonation product ordinarily contains various isomers such as 1,6-naphthalenedisulfonic acid, 2,6-naphthalenedisulfonic acid and 2,7-naphthalenedisulfonic acid, and it is very difficult to separate a specific naphthalenedisulfonic acid at a high purity from this reaction product mixture. Thus, only an extremely limited number of processes have been proposed for the separation and/or purification of naphthalenedisulfonic acids.

For example, as the known process, there can only be mentioned a process in which sodium 2,6-naphthalenedisulfonate is separated by utilizing the solubility difference among salts of naphthalenedisulfonic acids and a process in which aniline is added to a mixture of naphthalenedisulfonic acids to form aniline salts of naphthalenedisulfonic acids and separation is carried out by utilizing the solubility difference among the aniline salts.

A certain separation effect can be attained in these known processes, but they still involve defects or disadvantages to be eliminated.

More specifically, in the former process, since the solubility difference among isomers of naphthalenedisulfonic acid sodium salts is not conspicuous at room temperature, the solubility difference at elevated temperatures should be utilized. Accordingly, an apparatus capable of resisting high temperatures should be employed and, when an operation is conducted at high temperatures, it always involves risks.

In the latter process, since aniline, one of the organic solvents, is used for separation, the steps of recovering and purifying aniline are necessary and an increase in the costs of products is inevitably brought about. Therefore, this process is not a preferred one from an industrial viewpoint.

As will be apparent from the foregoing illustration, the known processes for separating specific naphthalenedisulfonic acids from disulfonation reaction mixtures have always involved one problem or another.

SUMMARY OF THE INVENTION

It is a primary object of the present invention to establish a process for separating one specific naphthalenedisulfonic acid from a mixture containing various naphthalenedisulfonic acids at a relatively low temperature without using an organic solvent.

Another object of the present invention is to provide a process for separating one specific naphthalenedisulfonic acid at a high purity from a mixture of naphthalenedisulfonic acid isomers.

In accordance with the present invention, these and other objects can be obtained by a process for separating one specific naphthalenedisulfonic acid from a reaction mixture obtained by disulfonation of naphthalene, which comprises adding water to said reaction mixture to adjust the sulfuric acid concentration in the mixture to 35 to 95% by weight, maintaining the temperature of the mixture at 0° to 80° C. and separating the precipitated crystal of said specific naphthalenedisulfonic acid.

According to the process of the present invention, a specific isomer of naphthalenedisulfonic acid can be separated at a high purity in the form of a free acid from a mixture of naphthalenedisulfonic acids which have been prepared according to specific reaction conditions known to favor the formation of a particular isomer.

Furthermore, in the process of the present invention, inorganic salts or organic solvents used in the conventional processes need not be used at all. The intended product can be easily obtained by the simple operation of diluting a reaction mixture obtained by disulfonation of naphthalene (within specific reaction conditions) with water to adjust the sulfuric acid concentration while controlling the temperature. No particular apparatus or equipment need be used for the separation. Moreover, when there is an equilibrium relation between naphthalenedisulfonic acid isomers, for example, between 2,6- and 2,7-naphthalenedisulfonic acids, by using the filtrate left after separation of 2,7-naphthalenedisulfonic acid as the diluting water for the subsequent separation cycle, 2,6-naphthalenedisulfonic acid in the filtrate can be isomerized to 2,7-naphthalenedisulfonic acid. Therefore, the conversion and effective utilization ratio can be remarkably enhanced.

DETAILED DESCRIPTION OF THE INVENTION

The separation process of the present invention will now be described in detail.

Any of the mixtures containing at least two isomers of naphthalenedisulfonic acid can be treated according to the process of the present invention. A reaction mixture obtained by disulfonation of naphthalene is a typical preferred example of such isomer mixture. Since the kinds and proportions of isomers of naphthalenedisulfonic acid contained in such reaction mixture can be appropriately changed depending on the conditions of the disulfonation reaction, it is preferred that a disulfonation product mixture containing the intended naphthalenedisulfonic acid isomer in a proportion as large as possible be prepared by the disulfonation reaction. For example, when separation of 1,6-naphthalenedisulfonic acid is intended, as is well known in the art, a sulfonating agent is used in an amount of 4 to 6 moles per mole of naphthalene and a reaction mixture obtained by conducting the reaction at a temperature of 40° to 100° C. is used.

Generally, this reaction mixture contains 20 to 40% by weight of 1,6-naphthalenedisulfonic acid and the sulfuric acid concentration in the reaction mixture is ordinarily 80 to 90% by weight, though the sulfuric acid concentration differs to some extent depending on the molar ratio of the sulfonating agent used.

In the process of the present invention, specific amounts of naphthalene and sulfuric acid are added together and allowed to react at a particular temperature for a particular length of time. The amounts of naphthalene and sulfuric acid chosen, as well as the temperature range and amount of time allowed for the reaction, are dependent upon the particular isomer of naphthalenedisulfonic acid which is to be separated away. The applicants have discovered that the optimum separation conditions are selected depending upon the types and proportions of isomers present in the starting reaction mixture. Separation of the intended naphthalenedisulfonic acid is carried out under conditions which are selected depending upon the types and proportions of isomers which are present. Therefore, if the applicants intend to separate away the isomer of, for example, 1,6-naphthalenedisulfonic acid, the reaction mixture will be prepared as shown in Example 1 of this application wherein 128 grams of naphthalene are added to 570 grams of 90% sulfuric acid, after which the disulfonation reaction is carried out at 80° C. for seven hours. The reaction conditions yield a reaction mixture which contains a relatively high proportional amount of the 1,6-naphthalenedisulfonic acid.

After this reaction mixture is obtained and contains the high percentage of 1,6-naphthalenedisulfonic acid, water is added to this reaction mixture to adjust the concentration to 35 to 90% by weight, preferably 45 to 60% by weight, and then the temperature is maintained at 0° to 80° C., preferably 20° to 60° C.

If the sulfuric acid concentration is lower than 35% by weight, the solubility of 1,6-naphthalenedisulfonic acid becomes greater and, therefore, it becomes more difficult to carry out the crystal separation.

If the sulfuric acid concentration is higher than 90% by weight, the solubility of 1,6-naphthalenedisulfonic acid is increased and the amount precipitated of 1,6-naphthalenedisulfonic acid is decreased.

When the temperature is maintained below 0° C., incorporation of other isomers takes place and results in reduction of the purity. When the temperature is maintained above 80° C., the amount precipitated of 1,6-naphthalenedisulfonic acid is decreased.

By the above-mentioned procedures, 1,6-naphthalenedisulfonic acid can be separated in the form of a high purity free acid crystal.

In the present invention, water to be used for adjustment of the sulfuric acid concentration includes not only ordinary water but also the filtrate left after filtration and separation of a crystal of the intended naphthalenedisulfonic acid.

When separation of 2,6-naphthalenedisulfonic acid and 2,7-naphthalenedisulfonic acid is intended, a reaction mixture obtained by carrying out the sulfonation reaction at a temperature of 130° to 180° C. by using a sulfonating agent in an amount of 3 to 6 moles per mole of naphthalene according to customary procedures is used. Generally, this reaction mixture contains 15 to 20% of 2,6-naphthalenedisulfonic acid and 25 to 35% of 2,7-naphthalenedisulfonic acid, based on the total weight of the reaction mixture, and the sulfuric acid concentration in the reaction mixture is 80 to 90% by weight.

When 2,6-naphthalenedisulfonic acid is separated from this reaction mixture, the reaction mixture is diluted with water to adjust the sulfuric acid concentration to 45 to 90% by weight, preferably 50 to 75% by weight. Then, the temperature is maintained at 0° to 70° C., preferably 20° to 50° C., to separate 2,6-naphthalenedisulfonic acid from the mixture.

When the sulfuric acid concentration is lower than 45% by weight, separation becomes difficult due to the high solubility of 2,6-naphthalenedisulfonic acid. If the sulfuric acid concentration is higher than 90% by weight, the solubility of 2,6-naphthalenedisulfonic acid becomes greater and the amount of crystals separated increases.

If the temperature is lower than 0° C., filtration becomes difficult and the number of isomers other than 2,6-isomer is increased. If the temperature is higher than 70° C., the amount precipitated of 2,6-naphthalenedisulfonic acid is decreased.

When separation of 2,7-naphthalenedisulfonic acid is intended, the disulfonation reaction between naphthalene and sulfuric acid is first carried out in order to obtain a reaction mixture which contains a large amount of the isomer which is to be separated out, i.e., 2,7-naphthalenedisulfonic acid. Therefore, these reaction conditions are similar to those within Examples 7-11 in the present application. About 128 grams of naphthalene are added to 300 grams of 98% sulfuric acid, and the disulfonation reaction is carried out at 170° C. for about six hours.

Thereafter, the sulfuric acid concentration in the reaction mixture is adjusted to 35 to 60% by weight, preferably 35 to 45% by weight. Then the temperature is maintained at 0° to 50° C., preferably 20° to 40° C.

If the sulfuric acid concentration is lower than 35% by weight, the solubility of 2,7-naphthalenedisulfonic acid is increased and results in the decrease of the precipitated amount. If the sulfuric acid concentration is higher than 50% by weight, the amount of the 2,6-isomer is increased.

When the temperature is lower than 0° C., the amount of the 2,6-isomer is increased and when the temperature is higher than 50° C., the solubility of 2,7- naphthalenedisulfonic acid is increased, resulting in a decrease of the precipitated amount.

As will be apparent from the foregoing illustration, in the process of the present invention, optimum separation conditions are selected depending upon the kinds and proportions of isomers present in the starting reaction mixture and separation of the intended naphthalenedisulfonic acid is carried out under the so-selected conditions.

Generally, a 2,7-naphthalenedisulfonic acid has a higher industrial value than 2,6-naphthalenedisulfonic acid. In the conventional processes, since both the 2,7- and 2,6-isomers are separated by utilizing the solubility difference between salts of the two isomers, the salt of 2,6-naphthalenedisulfonic acid having a lower solubility is first precipitated and the salt of 2,7-naphthalenedisulfonic acid is then precipitated from the filtrate after separation of the salt of the 2,6-isomer.

In contrast, according to the present invention, by selecting appropriate separation conditions, 2,7-naphthalenedisulfonic acid alone can be separated from the reaction mixture while leaving 2,6-naphthalenedisulfonic acid in the filtrate.

Moreover, since there is established an equilibrium relation between 2,6-naphthalenedisulfonic acid and 2,7-naphthalenedisulfonic acid as pointed out hereinabove, if the filtrate left after separation of 2,7-naphthalenedisulfonic acid is used for the subsequent cycle of separation as the diluting water, an excessive portion of 2,6-naphthalenedisulfonic acid can be isomerized to 2,7-naphthalenedisulfonic acid. Accordingly, the separation efficiency of 2,7-naphthalenedisulfonic acid can be further enhanced.

When a disulfonation reaction mixture is diluted with water to adjust the sulfuric acid concentration within the above-mentioned range, a part of the reaction mixture is collected as a sample in advance and the sulfuric acid concentration (before the dilution) is determined according to alkali titration. Based on the results of the titration, the amount of water necessary for lowering the sulfuric acid concentration to the above-mentioned predetermined level is calculated. The diluting water may be incorporated into the reaction mixture. Alternately, the reaction mixture may be incorporated into the diluting water.

Since heat is ordinarily generated at the diluting step, the diluting operation is carried out while conducting cooling according to a method in which water or a coolant is circulated in a jacket or hose line of a diluting tank or a method in which ice is added to the reaction mixture in an amount necessary for dilution. Simultaneously, the temperature of the diluted disulfonation reaction mixture is maintained at the predetermined level according to the particular isomer of naphthalenedisulfonic acid desired. The precipitated crystal of the intended naphthalenedisulfonic acid is recovered by filtration according to customary procedures. Thus, it is possible to obtain a particular isomer of naphthalenedisulfonic acid having a high purity.

Prior to the present process for the separation of isomers of naphthalenedisulfonic acids being specifically described by the following examples, it is to be understood that this invention is not limited to the particular amounts of components and reaction times disclosed since such processes may, of course, vary. It is also to be understood that the terminology utilized herein is for purposes of description of particular embodiments, and is not intended to be limiting since the scope of the present invention is intended to be limited only by the appended claims.

EXAMPLE 1

To 128 g of naphthalene was added 570 g of 98% sulfuric acid and the disulfonation reaction was carried out at 80° C. for 7 hours. The resulting disulfonation reaction mixture comprised 53.9% of sulfuric acid, 3.9% of water, 1.2% of 2,6-naphthalenedisulfonic acid, 3.1% of 2,7-naphthalenedisulfonic acid, 22.1% of 1,6-naphthalenedisulfonic acid, 13.2% of 1,7-naphthalenedisulfonic acid and 1.9% of $\beta$-naphthalenesulfonic acid based on the total weight of the reaction mixture.

The sulfuric acid concentration in the disulfonation reaction mixture was adjusted to 56% by weight by adding 270 ml of water to 693 g of the disulfonation reaction mixture. The precipitated disulfonic acids were completely dissolved by heat generated by the dilution. The mixture was cooled with water and the temperature was maintained at 35° C. The precipitated crystal was recovered by filtration to obtain 110 g of 1,6-naphthalenedisulfonic acid.

EXAMPLE 2

To 693 g of the disulfonation reaction mixture obtained in Example 1 was added 223 ml of water to adjust the sulfuric acid concentration to 60% by weight. The temperature was maintained at 50° C. and the precipitated crystal was recovered by filtration to obtain 76.5 g of 1,6-naphthalenedisulfonic acid having a purity of 97%.

EXAMPLE 3

To 693 g of the disulfonation reaction mixture obtained in Example 1 was added 133 ml of water to adjust the sulfuric acid concentration to 70% by weight, and the temperature was maintained at 75° C. Thus, 81 g of 1,6-naphthalenedisulfonic acid having a purity of 95.2% was obtained.

EXAMPLE 4

To 128 g of naphthalene was added 392 g of 98% sulfuric acid and the temperature was elevated to 160° C., and the reaction was carried out at this temperature for 6 hours. The resulting disulfonation reaction mixture comprised 35.7% of sulfuric acid, 8.5% of water, 16.0% of 2,6-naphthalenedisulfonic acid, 31.6% of 2,7-naphthalenedisulfonic acid, 3.2% of 1,6-naphthalenedisulfonic acid, 3.2% of 1,7-naphthalenedisulfonic acid and 1.7% of $\beta$-naphthalenesulfonic acid based on the total weight of the reaction mixture. To 520 g of the so-obtained disulfonation reaction mixture was added 44.6 ml of water to adjust the sulfuric acid concentration to 68% by weight. The precipitated disulfonic acids were dissolved and the temperature was lowered to room temperature. The precipitated crystal was recovered by filtration to obtain 40 g of 2,6-naphthalenedisulfonic acid at a purity of 83%.

EXAMPLE 5

To 520 g of the disulfonation reaction mixture obtained in Example 4 was added 82.2 ml of water to adjust the sulfuric acid concentration to 60% by weight. The mixture was cooled to 30° C. and the precipitated crystal was recovered by filtration to obtain 38 g of 2,6-naphthalenedisulfonic acid having a purity of 96%.

EXAMPLE 6

To 520 g of the disulfonation reaction mixture obtained in Example 4 was added 180 ml of water to adjust the sulfuric acid concentration to 45% by weight. The mixture was cooled to 23° C. and the precipitated crystal was recovered by filtration to obtain 60 g of 2,7-naphthalenedisulfonic acid having a purity of 97%.

EXAMPLES 7 to 11

To 128 g of naphthalene was added 300 g of 98% sulfuric acid and the disulfonation reaction was carried out at 170° C. for 6 hours. The reaction mixture was cooled and water was added so as to adjust the sulfuric acid concentration as shown in Table 1. The temperature was maintained at 25° C. and the precipitated crystal was recovered by filtration. The amount obtained and purity of the recovered crystal of 2,7-naphthalenedisulfonic acid are shown in Table 1.

TABLE 1

| | Example 7 | Example 8 | Example 9 | Example 10 | Example 11 |
|---|---|---|---|---|---|
| Sulfuric acid concentration (% by weight) | 30 | 35 | 40 | 42 | 45 |
| Precipitation ratio (%) of 2,7-naphthalenedisulfonic acid | 0 | 15.6 | 40.4 | 60 | 70 |
| Purity (%) of 2,7-naphthalenedisulfonic acid | — | 97 | 67 | 60 | 58 |

As will be apparent from the results shown in Table 1, as the sulfuric acid concentration is lowered, the precipitation ratio is reduced. However, as the sulfuric acid concentration is increased, the purity is reduced.

EXAMPLE 12

To 128 g of naphthalene was added 392 g of 98% sulfuric acid and the reaction was carried out at 130° C. for 1 hour. Then the temperature was elevated to 190° C. and the reaction was further conducted at this temperature for 9 hours to obtain 520 g of a disulfonation reaction mixture. The disulfonation product in this reaction mixture included 35.7 mole % of 2,6-naphthalenedisulfonic acid and 40.0 mole % of 2,7-naphthalenedisulfonic acid, and the sulfuric acid concentration in this reaction mixture was 79.8% by weight.

To this disulfonation reaction mixture was added 63.2 ml of water at a temperature below 110° C. to adjust the sulfuric acid concentration to 63% by weight. Then the temperature was maintained at 60°±2° C. for 2 hours and the precipitated crystal was recovered by filtration to obtain 2,6-naphthalenedisulfonic acid having a purity of 85.0% in a yield of 82.4%.

To 388 g of the filtrate was added 80 ml of water while the temperature was maintained below 50° C. Thus, the sulfuric acid concentration was adjusted to 50% by weight. The mixture was allowed to stand still at 20°±2° C. for 2 hours and the precipitated crystal was recovered by filtration to obtain 2,7-naphthalenedisulfonic acid having a purity of 89.2% in a yield of 56.2%.

EXAMPLE 13

To 291 g of a disulfonation reaction mixture containing 30.7 mole % of 2,6-naphthalenedisulfonic acid and 57.9 mole % of 2,7-naphthalenedisulfonic acid and having a sulfuric acid concentration of 89.4% by weight, which was contained in the same manner as described in Example 12, 106.5 g of water was added to adjust the sulfuric acid concentration to 56.6% by weight. The temperature of the mixture was maintained at 23°±2° C. for 2 hours and the precipitated crystal was recovered by filtration to obtain 2,7-naphthalenedisulfonic acid having a purity of 88.6% in a yield of 45.5%.

EXAMPLE 14

A disulfonation reaction mixture containing 29.1 mole % of 2,6-naphthalenedisulfonic acid and 61.0 mole % of 2,7-naphthalenedisulfonic acid was prepared in the same manner as described in Example 12, and 98.8 g of water was added to 251 g of this disulfonation reaction mixture to adjust the sulfuric acid concentration to 50.6% by weight. The temperature of the mixture was maintained at 25°±2° C. for 2 hours. The precipitated crystal was recovered by filtration to obtain 2,7-naphthalenedisulfonic acid having a purity of 88.5% in a yield of 53.5%.

EXAMPLE 15

A disulfonation reaction mixture containing 22.7 mole % of 2,6-naphthalenedisulfonic acid and 58.7 mole % of 2,7-naphthalenedisulfonic acid was prepared in the same manner as described in Example 12 and 175 g of water was added to 526 g of this reaction mixture to adjust the sulfuric acid concentration to 48.3% by weight. The mixture was allowed to stand still at 20°±2° C. for three hours. The precipitated crystal was recovered by filtration to obtain 2,7-naphthalenedisulfonic acid having a purity of 90.5% in a yield of 65%.

EXAMPLE 16

The filtrate left after separation of 2,7-naphthalenedisulfonic acid in Example 15 was concentrated to adjust the sulfuric acid concentration to 58.6% by weight, and the temperature of the mixture was maintained at 65°±2° C. for 2 hours. The precipitated crystal was recovered by filtration to obtain 2,6-naphthalenedisulfonic acid having a purity of 92.2% in a yield of 88.3%.

EXAMPLE 17

A disulfonation reaction mixture containing 24.3 mole % of 2,6-naphthalenedisulfonic acid and 55.6 mole % of 2,7-naphthalenedisulfonic acid was prepared in the same manner as described in Example 12 and 357 g of water was added to 780 g of this reaction mixture to adjust the sulfuric acid concentration to 40% by weight. The mixture was allowed to stand still at 25°±2° C. for 3 hours and the precipitated crystal was recovered by filtration to obtain 2,7-naphthalenedisulfonic acid having a purity of 92.6% in a yield of 52%.

EXAMPLE 18

A disulfonation reaction mixture containing 25.6 mole % of 2,6-naphthalenedisulfonic acid and 53.4 mole% of 2,7-naphthalenedisulfonic acid was prepared in the same manner as described in Example 12, and 835 g of water was added to 1981 g of this reaction mixture to adjust the sulfuric acid concentration to 41% by weight. The mixture was allowed to stand at 20°±2° C. for 3 hours and the precipitated crystal was recovered by filtration to obtain 2,7-naphthalenedisulfonic acid having a purity of 100% in a yield of 65.0%.

The instant invention has been described in general and also with respect to specific examples herein in what is considered to be the most practical and preferred methods for carrying out the invention. It is recognized, however, that departures may be made therefrom which are within the scope of the invention, and that obvious modifications will occur to a person of ordinary skill in the art.

What is claimed:

1. A process for separating 2,6-naphthalenedisulfonic acid from a reaction mixture resulting from the disulfonation of naphthalene, which comprise the steps of:
   (a) disulfonating naphthalene under β,β-disulfonation reaction conditions in order to obtain a reaction mixture containing predominantly 2,6-naphthalenedisulfonic acid and 2,7-naphthalenedisulfonic acid therein;
   (b) adding water to said reaction mixture obtained by said disulfonation of naphthalene in order to adjust to 50 to 70% by weight the sulfuric acid concentration in said reaction mixture;
   (c) maintaining the reaction mixture at a temperature of 0° to 70° C.; and
   (d) separating away precipitated crystals of 2,6-naphthalenedisulfonic acid.

2. A process as in claim 1 wherein said reaction mixture is maintained at a temperature of 0° to 70° C.

3. A process as in claim 1 wherein said sulfuric acid concentration is adjusted to 50 to 75% by weight and said reaction mixture is maintained at a temperature of 20° to 50° C.

4. A process for separating 1,6-naphthalenedisulfonic acid from a reaction mixture resulting from the disulfonation of naphthalene, which comprises the steps of:
   (a) disulfonating naphthalene under α,β-disulfonation reaction conditions, in order to obtain a reaction mixture containing predominantly 1,6-naphthalenedisulfonic acid and 1,7-naphthalenedisulfonic acid and minor amounts of 2,6- and 2,7-naphthalenedisulfonic acids;
   (b) adding water to said reaction mixture obtained by disulfonation of naphthalene in order to adjust to 35 to 90% by weight of sulfuric acid concentration in said reaction mixture;
   (c) maintaining said reaction mixture at a temperature of 0° to 80° C.; and
   (d) separating away precipitated crystals of 1,6-naphthalenedisulfonic acid.

5. A process as in claim 4 wherein said sulfuric acid concentration is adjusted to 45 to 60% by weight.

6. A process as in claim 4 wherein said reaction mixture is maintained at a temperature of 20° to 60° C.

7. A process as in claim 4 wherein said sulfuric acid concentration is adjusted to 45 to 60% by weight, and said reaction mixture is maintained at a temperature of 20° to 60° C.

8. A process for separating 2,7-naphthalenedisulfonic acid from a reaction mixture resulting from the disulfonation of naphthalene, which comprises the steps of:
   (a) disulfonating naphthalene under β,β-disulfonation reaction conditions in order to obtain a resulting reaction mixture containing predominantly 2,6-naphthalenedisulfonic acid and 2,7-naphthalenedisulfonic acid therein;
   (b) adding water to said reaction mixture obtained by said disulfonation of naphthalene in order to adjust to 35 to 45% by weight the sulfuric acid concentration within said reaction mixture;
   (c) maintaining said reaction mixture at a temperature of 0° to 50° C.; and
   (d) separating away precipitated crystals of 2,7-naphthalenedisulfonic acid.

9. A process according to claim 8 wherein said reaction mixture is maintained at a temperature of 20° to 40° C.

10. A process as in claim 8 wherein said sulfuric acid concentration is adjusted to 35 to 45% by weight and the reaction mixture is maintained at a temperature of 20° to 40° C.

* * * * *